US00PP27316P3

(12) United States Plant Patent
Dobres

(10) Patent No.: US PP27,316 P3
(45) Date of Patent: Oct. 25, 2016

(54) ***PENSTEMON* PLANT NAMED 'NOVAPENPUR'**

(50) Latin Name: *Penstemon barbatus*
Varietal Denomination: Novapenpur

(71) Applicant: CP DELAWARE, INC., Wilmington, DE (US)

(72) Inventor: Michael S. Dobres, Philadelphia, PA (US)

(73) Assignee: CP Delaware Inc., Wilmington, DE (US)

( * ) Notice: Subject to any disclaimer, the term of this patent is extended or adjusted under 35 U.S.C. 154(b) by 383 days.

(21) Appl. No.: 13/998,817

(22) Filed: Dec. 11, 2013

(65) Prior Publication Data

US 2015/0163983 P1 Jun. 11, 2015

(51) Int. Cl.
*A01H 5/02* (2006.01)

(52) U.S. Cl.
USPC ..... Plt./465

(58) Field of Classification Search
USPC ..... Plt./465
See application file for complete search history.

(56) References Cited

U.S. PATENT DOCUMENTS

| | | | |
|---|---|---|---|
| PP23,064 | P2 | 9/2012 | Lubbe |
| PP23,065 | P2 | 9/2012 | Lubbe |
| PP23,066 | P2 | 9/2012 | Lubbe |
| PP23,067 | P2 | 9/2012 | Lubbe |
| PP23,089 | P2 | 9/2012 | Lubbe |
| PP23,098 | P2 | 10/2012 | Lubbe |

*Primary Examiner* — Keith Robinson
(74) *Attorney, Agent, or Firm* — Buchanan Ingersoll & Rooney PC

(57) ABSTRACT

The new *Penstemon* plant was created by the crossing of parent plants which had been studied in the hope that they might provide desired characteristics. Attractive dark-purple blossoms with a white throat are formed in the absence of a vernalization requirement for flowering. An upright compact mounding growth habit is displayed. The plant is well suited for providing attractive ornamentation in the landscape.

1 Drawing Sheet

Botanical/commercial classification: *Penstemon barbatus/Penstemon* Plant.

Varietal denomination. cv. Novapenpur.

SUMMARY OF THE INVENTION

*Penstemon* plants, sometimes known as Beard Tongue, are herbaceous perennials which provide colorful flowers during the summer.

The new *Penstemon* plant of the present invention was created at West Grove, Pa., U.S.A., by artificial pollination wherein two parents were crossed which previously had been studied in the hope that they would provide the desired characteristics. Each parent was acquired as a seed mixture. The female parent (i.e., seed parent) was *Penstemon barbatus* 'Rondo' (non-patented). The male parent (i.e., pollen parent) was *Penstemon barbatus* 'Navigator' (non-patented).

The parentage of the new variety can be summarized as follows:

'Rondo'×'Navigator'.

The seeds resulting from the above pollination were sown and small plants were obtained which were physically and biologically different from each other. Selective study resulted in the identification of a single plant of the new cultivar.

It was found that the new *Penstemon* plant displays the following combination of characteristics:

(a) displays an upright compact growth habit with strong basal branching, (b) is lacking a vernalization requirement for flowering, (c) forms attractive dark-purple blossoms with a white throat, and (d) is well suited for providing attractive ornamentation in the landscape.

During observations to date, the plant has been found to be hardy in U.S.D.A. Hardiness Zone No. 6. No further definitive hardiness information has been obtained. Trimming of the plant tends to produce further flowering.

The new cultivar well meets the needs of the horticultural industry and can be grown to advantage as a perennial garden plant to provide colorful ornamentation. For instance, it can be grown in parks, gardens and residential settings.

Plants of the new cultivar can be readily distinguished from other *Penstemon* cultivars including its parents. More specifically, 'Rondo' exhibits a considerably taller growth habit, and 'Navigator' commonly displays a wide mix of colored blossoms.

When compared to the 'Purple Riding Hood' cultivar (U.S. Plant Pat. No. 23,067), the new cultivar displays considerably more basal branching. When compared to the 'Novapenpin' cultivar (U.S. Plant Pat. No. 26,701), the new cultivar displays dark purple blossoms as opposed to the bright pink blossoms of 'Novapenpin'.

The rooting of cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novapenpur', and will be marketed under the PURPLE ROCK CANDY Trademark.

BRIEF DESCRIPTION OF THE PHOTOGRAPH

The accompanying photograph illustrates a typical flowering plant of the new cultivar in color as nearly true as it is reasonably possible to make in a color illustration of this nature. The plant was approximately one year of age and was being grown outdoors in full sun late in the season (during September 2013) at West Grove, Pa., U.S.A. The plant had been asexually reproduced by the rooting of a cutting, and had been trimmed to induce further flowering. The blossom coloration is believed to be influenced by the extreme lateness in the season when growing outdoors and the advanced age of the depicted blossoms which imparted some fading in coloration.

DETAILED BOTANICAL DESCRIPTION

The following is a detailed description while observing one-year-old plants of the new cultivar that were produced by the rooting of cuttings. Such plants were being grown during September 2013 in one-gallon containers under greenhouse conditions at West Grove, Pa., U.S.A. The chart used in the identification of color is The R.H.S. Colour Chart (1995 Edition) of The Royal Horticultural Society, London, England. Common color terms are to be accorded their customary dictionary significance.

Botanical classification: *Penstemon barbatus*, cv. 'Novapenpur.'.

*Parents*.—Cross of seed mixtures of *Penstemon barbatus* 'Rondo' and 'Navigator'.

*Plant type*.—Herbaceous perennial.

Plant:

*Growth habit*.—Upright and compact.

*Height*.—Approximately 12 to 18 cm on average when mature. During observations, the 'Rondo' parent assumed a height of approximately 24 inches.

*Spread*.—Approximately 12 to 18 inches on average when mature.

*Branching*.—Commonly approximately 7 lateral stems arise at the base. During observations, this compares to approximately 2 or 3 basal branches for the 'Purple Riding Hood' cultivar.

*Branch length*.—Commonly approximately 24 cm on average.

*Branch diameter*.—Commonly approximately 4 mm on average.

*Stem strength*.—Relatively strong.

*Stem color*.—Near Green Group 138B.

*Stem texture*.—Smooth.

*Internode length*.—Commonly approximately 3 cm.

*Roots*.—Fibrous network, with the rooting of cuttings commonly commencing in approximately 16 days on average, and a fully rooted plant commonly being produced in approximately 35 days on average.

Foliage:

*Arrangement*.—Opposite.

*Shape*.—Lanceolate.

*Apex*.—Truncate.

*Base*.—Acuminate.

*Length*.—Commonly approximately 9 cm on average.

*Width*.—Commonly approximately 2.5 cm on average.

*Texture*.—Smooth on the upper and under surfaces.

*Color*.—On the upper surface near Green Group 137A, and on the lower surface near Green Group 137B.

*Margins*.—Entire.

*Venation*.—Arcuate venation with a color near Yellow-Green Group 145C.

*Petiole length*.—Commonly approximately 3.2 mm on average.

*Petiole width*.—Commonly approximately 3.2 mm on average.

*Petiole texture*.—Smooth, glabrous.

*Petiole color*.—Near Yellow-Green Group 145C.

Inflorescence:

*Season*.—The natural flowering season when grown outside primarily is approximately May to July in West Grove, Pa. Such flowering season can be further extended with trimming.

*Type*.—Single, arranged on terminal racemes, and with flowers mostly facing outwards.

*Buds*.—Ovoid, smooth/glabrous in texture, approximately 2.2 cm in length on average just before opening, approximately 8 mm in diameter, and near Purple Group 79A in coloration.

*Quantity*.—Free-flowering, commonly with approximately 78 flowers on average developing per inflorescence.

*Flower diameter*.—Approximately 2.3 cm on average.

*Flower length*.—Approximately 2.7 cm on average.

*Flower longevity*.—Commonly approximately 7 days on average.

*Petal number*.—Five.

*Petal arrangement*.—Petals fused into a tube, bi-labiate, upper lip with two upper petals, and lower lip with three lower petals.

*Petal length*.—Approximately 9 mm on average.

*Petal width*.—Approximately 7 mm on average.

*Petal shape*.—Substantially round.

*Petal apex*.—Rounded.

*Petal base*.—Rounded.

*Petal margin*.—Entire.

*Petal texture*.—Smooth on upper and under surfaces.

*Petal color*.—Upper surface: when opening near Violet Group 79A, and when fully open near Purple Group 83A. Lower surface: when opening near Purple Group 79B, and when fully open near Violet Group 83B.

*Throat color*.—The tube commonly is near White Group 155A.

*Sepal arrangement*.—Five sepals in a single whorl, and with salverform calyx.

*Sepal shape*.—Broadly lanceolate.

*Sepal length*.—Approximately 5 mm on average.

*Sepal diameter*.—Approximately 4 mm on average.

*Sepal apex*.—Pointed.

*Sepal base*.—Truncate.

*Sepal margin*.—Entire.

*Sepal texture*.—Smooth on upper and under surfaces.

*Sepal color*.—Near Green Group 138A on the upper surface and near Green Group 143A on the under surface.

*Stamen number*.—Four.

*Stamen length*.—Approximately 2.5 cm on average.

*Stamen diameter*.—Approximately 0.79 mm on average.

*Anther opening*.—Tend to dehisce the full length across the connective and to spread widely apart.

*Anther number*.—Four.
*Anther length*.—Approximately 4 mm on average.
*Anther diameter*.—Approximately 0.79 mm on average.
*Anther shape*.—Horn shaped with long hairs.
*Anther color*.—Near Greyed-Yellow Group 160D.
*Filaments*.—Commonly approximately 1.9 cm in length on average, and near White Group 155D in coloration.
*Pollen*.—Present in a moderate quantity, and near Yellow Group 2D in coloration.
*Pistil number*.—One.
*Pistil length*.—Approximately 2 cm on average.
*Style number*.—One.
*Style length*.—Approximately 1.5 cm on average.
*Style color*.—Near White Group 155D at the apex and base, commonly with some Purple Group 77A at the center portion.
*Stigma color*.—Near White Group 155D.
*Stigma shape*.—Undifferentiated.
*Seeds/fruit*.—Have not been observed.
*Fragrance*.—None detected.
*Peduncle length*.—Approximately 3 to 4 cm on average.
*Peduncle diameter*.—Approximately 2 mm on average.
*Peduncle aspect*.—Commonly approximately 80 degrees.
*Peduncle texture*.—Smooth.
*Peduncle strength*.—Relatively strong.
*Peduncle color*.—Near Green Group 143C.
*Pedicel length*.—Approximately 5 mm on average.
*Pedicel diameter*.—Approximately 1 mm on average.
*Pedicel aspect*.—Commonly approximately 45 degrees.
*Pedicel strength*.—Relatively strong.
*Pedicel color*.—Near Green Group 143C.
*Ovary size*.—Approximately 3.2 mm on average.
*Ovary color*.—Near Yellow-Green Group 145A.

Disease resistance: The tolerance/susceptibility to diseases and pests common to *Penstemon* plants appears to be typical during observations to date.

Plants of the 'Novapenpur' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Penstemon* plant having the following combination of characteristics:

(a) displays an upright compact growth habit with strong basal branching,
(b) is lacking a vernalization requirement for flowering,
(c) forms attractive dark-purple blossoms with a white throat, and
(d) is well suited for providing attractive ornamentation in the landscape;

substantially as illustrated and described.

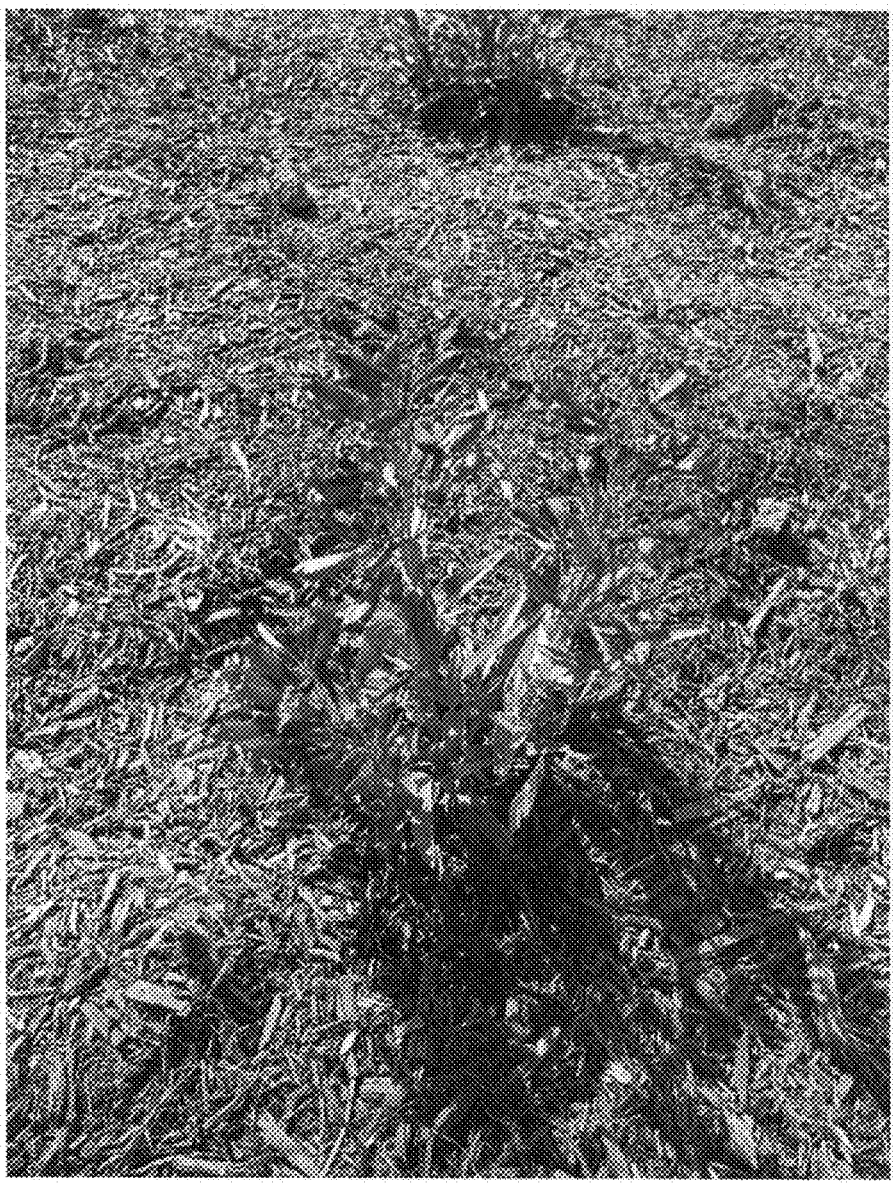

* * * * *